United States Patent [19]

Gonus et al.

[11] Patent Number: 5,401,862
[45] Date of Patent: Mar. 28, 1995

[54] PROCESS FOR DECOLORING FATTY ACID ESTERS

[75] Inventors: Philippe Gonus, Chesalles/Oron; Hans-Juergen Wille, Villeneuve, both of Switzerland

[73] Assignee: Nestec S.A., Vevey, Switzerland

[21] Appl. No.: 7,120

[22] Filed: Jan. 21, 1993

[30] Foreign Application Priority Data

Feb. 19, 1992 [EP] European Pat. Off. ............ 92102742

[51] Int. Cl.$^6$ .............................. C11B 3/10; C11B 3/12
[52] U.S. Cl. ........................................ 554/191; 554/175
[58] Field of Search .......................................... 554/191

[56] References Cited

U.S. PATENT DOCUMENTS

| | | | |
|---|---|---|---|
| 3,369,993 | 2/1968 | Mills et al. | 208/26 |
| 3,787,330 | 1/1974 | Sugahara et al. | 252/450 |
| 3,955,004 | 5/1976 | Strauss et al. | 426/254 |
| 4,781,864 | 11/1988 | Pryor et al. | 260/420 |

FOREIGN PATENT DOCUMENTS

| | | |
|---|---|---|
| 079799 | 5/1983 | European Pat. Off. . |
| 0108571 | 5/1984 | European Pat. Off. . |
| 2080350 | 2/1982 | United Kingdom . |

OTHER PUBLICATIONS

Angelin, et al., "Oil Extraction and Refining From Somalu Papaya Seeds," Ital. delle Sostanze Grasse, vol. 67, May (1990) pp. 257–258.

Cho-Ah-Ying, et al., "Adsorptive Removal of Sulfur From Canola Oil," Pat. Sci. Technol., 93 Jah, No. 4, (1991), pp. 132–135.

Primary Examiner—Paul J. Killos
Assistant Examiner—Dwayne C. Jones
Attorney, Agent, or Firm—Vogt & O'Donnell

[57] ABSTRACT

Fatty acid esters, particularly those suitable for use in foods and cosmetics, are decolored by passing a solution of a fatty acid ester dissolved in an apolar solvent through particulate montmorillonite which is in admixture with particulate silica gel and/or active carbon. The solution passed through the column is obtained and the solvent is eliminated from the ester.

23 Claims, No Drawings

PROCESS FOR DECOLORING FATTY ACID ESTERS

BACKGROUND OF THE INVENTION

This invention relates to a process for decoloring a fatty acid ester, more particularly a special oil, intended for inclusion in the composition of food or cosmetic products.

In the majority of cases, the crude oils extracted by pressing or with solvents cannot be used as such in food or cosmetic products. They contain impurities which have to be eliminated by preliminary refining. The refining process generally comprises four successive steps, namely, acid degumming, alkaline neutralization, decolorization and, finally, deodorization. In certain particular cases of strongly colored oils which are intended for specific applications, for example in cosmetics, which require intensive decolorization, the conventional refining process, which comprises contacting with bentonite or acid-activated montmorillonite in vacuo in the presence of heat, followed by filtration, does not enable the level of decolorization required for the application envisaged to be achieved.

An improved decolorization process known as "chromatographic" decolorization comprises diluting the oil in an apolar solvent and adsorbing the impurities by contacting the solution with a solid adsorbent in a column. One such process is described, for example, in European patent application Publication No. 0 108 571, which relates in particular to the stabilization and decolorization of fish oils. In this process, a fish oil rich in polyunsaturated fatty acids is hydrogenated in the presence of a catalyst and is then decolorized in solution using a solid adsorbent, such as silica gel, activated alumina, aluminium silicate or activated clay, by successive passages of the solution through a column containing the adsorbent.

SUMMARY OF THE INVENTION

It has now surprisingly been found that the use of an adsorbent mixture of montmorillonite clay and silica gel or active carbon in a decolorization process by passage through a column of adsorbent material leads to the almost complete decolorization of oils hitherto impossible to decolorize to a satisfactory degree by the conventional decolorization processes mentioned above.

The process according to the invention, in which a fatty acid ester dissolved in an apolar solvent is passed through a column filled with adsorbent and the solvent is subsequently eliminated, is characterized in that a mixture based on montmorillonite containing silica gel and/or active carbon as adsorbent is used.

In a preferred embodiment, the adsorbent is a mixture containing from 10 to 60% by weight montmorillonite and up to 80% by weight silica gel. It may consist solely of these two constituents, for example approximately 50% by weight of silica gel and approximately 50% by weight of montmorillonite.

In one particularly preferred variant, the adsorbent additionally contains 30 to 60% by weight active carbon. In another particularly advantageous embodiment, the adsorbent mixture contains 30 to 80% by weight active carbon and 20 to 70% by weight montmorillonite. The present invention also relates to a food or cosmetic composition containing a compound decolored by the process according to the invention.

DETAILED DESCRIPTION OF THE INVENTION

In accordance with the invention, the montmorillonite may be in the form of a powder having a particle size of, for example, 5 to 60 microns or in the form of granules, for example from 60 to 250 microns in diameter. The silica gel may be in the form of granules, for example from 60 to 500 microns in diameter. The active carbon may consist of granules, for example 100 to 500 microns in diameter, with pores, for example a few microns in size, forming cells at the surface of the granules, and the mixture may contain the active carbon in the form of granules and the montmorillonite in powder form.

The montmorillonite may be in the form of a powder or granules or in the form of a mixture preferably containing 40 to 60% by weight powder and 60 to 40% by weight granules, including when the absorbent mixture contains from 10% to 60% by weight montmorillonite and up to 80% by weight silica gel and when that mixture is approximately 50% by weight of each.

The adsorbent mixture may additionally contain a filler as filtration additive, for example a diatomaceous earth, for example diatomite or perlite, in a quantity of up to 30% by weight.

The compounds to be decolorized by the process according to the invention may be animal oils, for example fish oil, or vegetable oils, for example oil from cumin seeds, *Lesquerella, Hevea brasiliensis*, elder, calendula, kiwi, bilberry, coffee, or oils of biosynthetic origin, for example from envelopes of yeast, or even of synthetic origin, for example a fatty acid butanediol diester.

To carry out the process, the compound to be treated, which has been conventionally refined by degumming, neutralization and decolorization as described above, is dissolved in an apolar solvent, for example an aliphatic hydrocarbon of food quality, preferably n-hexane, in a ratio by weight of compound to solvent of 1:2 to 1:16 and preferably of the order of 1:9. For dissolution, the compound may have to be liquefied by heating, and the solution should be clear. The ratio of compound to solvent is determined by the nature of the compound to be treated and is the result of a compromise between a minimum quantity of solvent, which then has to be eliminated, and sufficient dilution of the compound for the solution to be substantially apolar.

The solution is then passed through a column filled with the adsorbent mixture by gravimetry, preferably using a ratio by weight of fat to adsorbent of 0.5:1 to 5:1, for example 2:1, under a low or medium pressure, for example up to 1.5 bar, depending on the type of column and the particle size distribution of the adsorbent used.

The columns used may be inter alia columns from 27 to 225 mm in diameter and from 10 to 100 cm in height, short columns of relatively large diameter being preferred. Columns of which the diameter-to-height ratio is less than 1:2, enabling a fine-particle adsorbent to be used and low operating pressures, for example below about 0.2 bar, preferably are employed. The time taken by the solution to pass through the column is, for example, 15 to 60 minutes per liter of solution for approximately 50 g of adsorbent.

After percolation, the column is rinsed with solvent, preferably with a volume of solvent corresponding to approximately 25% of that of the solution. After the liquids have been combined, the solvent is eliminated, for example by evaporation in vacuo.

A cosmetic composition according to the invention will contain, for example, decolorized oils of cumin, calendula, bilberry, elder, coffee, kiwi, *Hevea brasiliensis* or a butanediol diester in a cream and oil of *Lesquerella* in a lipstick for their interesting cosmetic properties.

A dietetic food composition according to the invention will contain, for example, decolorized oils of bilberry, elder, kiwi or fish as fatty acid source of the *omega* 3 series. A dietetic composition according to the invention suitable for use in human or animal dietetics may contain, for example, a decolorized butanediol diester, as a substitute for fats, non-assimilable by the organism.

EXAMPLES

The invention is illustrated by the following Examples. In the Examples:

Parts and percentages are by weight, unless otherwise indicated.

The analyses conducted to determine the quality of the products and the level of decolorization are as follows:

FFA: free fatty acids expressed in % oleic acid;

POV: peroxide index in milliequivalent g oxygen/kg

Y(yellow), R(red), N(neutral): colorimetric units measured on the Lovibond scale (optical path of cell 12.7; 25.4 or 133.35 mm).

The experimental conditions for all the Examples are as follows:

The adsorbent is prepared by dry mixing its constituents in a container, optionally in vacuo, until a homogeneous mixture is obtained. The solvent is added and the whole is vigorously mixed for 2 to 3 minutes in a vacuum, for example a water jet vacuum, of 15 to 30 bar to degas the adsorbent which has an apparent density of approximately 0.4 to 0.5 kg/dm$^3$.

To prepare the column, which is provided with a filter plate at its base, n-hexane is initially introduced to purge the column, after which the column is filled with the adsorbent suspended in n-hexane.

The oil or fat, if necessary melted beforehand, is diluted in the n-hexane to form a perfectly clear solution. The solution is then percolated through the column over a period of 15 to 60 minutes, if necessary under a pressure of 0.2 to 1.5 bar (relative to the ambient pressure), using 1 liter of solution to 50 g adsorbent, depending on the type of column, after which, the column is rinsed with a volume of n-hexane corresponding to ¼ of the volume of the solution to be decolorized. After the liquids have been combined, the n-hexane is removed by evaporation in vacuo in a rotary evaporator. The n-hexane may be recycled and used to dissolve more of the fat.

The following adsorbents are used:

a: silica gel having a particle size distribution of 200 to 500μ b: powder-form montmorillonite, 5–50μ c: granulated montmorillonite, 150–250μ d: granulated silica gel, 63–200μ e: granulated silica gel, 100–400μ f: granulated active carbon, 100–500μ with cells a few μ in size at its surface g: diatomaceous earth, 10–100μ.

Decolorization in the case of conventional refining comprises contacting the solution with 0.5–3% by weight activated montmorillonite in a vacuum of 1 to 2 mbar at a temperature of 80° to 100° C., followed by filtration in a filter press.

Examples 1–2

The parameters of the process and the results are set out in Table 1 below for cumin seed oil which has the following fatty acid composition:

| Fatty acids | % |
| --- | --- |
| C16:0 | 4.3 |
| C18:0 | 1.1 |
| C18:1, Δ6 (petroselenic) and Δ9 | 59.9 |
| C18:2 | 33.4 |
| Others | 1.3 |

TABLE 1

| Example | Comparison 1 | Comparison 2 | 1 | 2 |
| --- | --- | --- | --- | --- |
| Sample (g) | After conventional decolorization | 150 | 150 | 150 |
| n-Hexane (ml) | | 450 | 450 | 450 |
| Adsorbent (type) | | a | a + b | a + b + c |
| Proportions (%) of the components of the adsorbent | | 100 | a:80 b:20 | a:50 b:20 c:30 |
| Quantity (g) | | 75 | 75 | 75 |
| Type of column | | Glass | Glass | Glass |
| Diameter (mm) | | 27 | 27 | 27 |
| Height (cm) | | 25 | 25 | 25 |
| Pressure (bar) | | Ambient | 0.2 | 0.2 |
| FFA (% oleic acid) | 0.1 | 0.05 | 0.05 | 0.04 |
| POV (meqO$_2$kg) | 0.86 | 0.75 | 0.26 | 0.33 |
| Color Y (25.4 mm cell) | 68 | 39 | 3.7 | 3.6 |
| R | 8.8 | 3.4 | 1 | 0.8 |

It can be seen that the treatment with an adsorbent mixture of silica gel and montmorillonite provides for better elimination of the peroxides and produces a significant improvement in decolorization by comparison with the starting product, which has been conventionally decolored (Comparison 1), and by comparison with the use of silica gel on its own (Comparison 2).

In addition, conventional decolorization is extremely slow which is due to solidification of the montmorillonite in the presence of solvent.

Examples 3–7

The parameters of the process and the results are set out in Table 2 below for *Lesquerella* seed oil which has the following fatty acid composition:

| Fatty acids | % |
| --- | --- |
| C16:0 | 2.1 |
| C16:1 | 1.5 |
| C18:0 | 3.2 |
| C18:1 | 23.2 |
| C18:2 | 9.7 |
| C18:3α | 15.1 |
| C20:1 | 1.5 |
| C20:1 (14-OH), lesquerolic | 43.3 |
| Others | 0.4 |

This oil is characterized by the fact that it continues a large quantity of hydroxylated lesqueolic acid which makes it difficult to decolor by the conventional method.

TABLE 2

| Example | Comparison 3 | Comparison 4 | 3 | 4 |
| --- | --- | --- | --- | --- |
| Sample (g) | After | After | 50 | 50 |

TABLE 2-continued

| Example | Comparison 3 | Comparison 4 | 3 | 4 |
|---|---|---|---|---|
| n-Hexane (ml) | 1 | 2 | 500 | 800 |
| Adsorbent (type) | conventional decolorization | conventional decolorizations | a + b + c | a + b + c + d |
| Proportions (%) of the components of the adsorbent | | | a:50 b:20 c:30 | a:25 b:25 c:25 d:25 |
| Quantity (g) of adsorbent | | | 50 | 50 |
| Type of column | | | Glass | Glass |
| Diameter (mm) | | | 27 | 27 |
| Height (cm) | | | 25 | 25 |
| Pressure (bar) | | | 0.2 | 0.2 |
| Color      Y (12.7 mm  R cell)       N | 68 12.6 2.5 | 69 11.9 2.6 | 35.5 1.4 0.2 | 17.4 1.1 0.7 |

| Example | 5 | 6 | 7 |
|---|---|---|---|
| Sample (g) | 50 | 50 | 515 |
| Hexane (ml) | 500 | 500 | 5000 |
| Adsorbent (type) | a + b + c + d | e + b | d + b |
| Proportions of the components of the adsorbent | a:25 b:25 c:25 d:25 | e:50 b:50 | d:50 b:50 |
| Quantity (g) of adsorbent | 50 | 50 | 600 |
| Type of column | Glass | Glass | Steel |
| Diameter (mm) | 50 | 50 | 125 |
| Height (cm) | 10 | 10 | 15 |
| Pressure (bar) | Ambient | Ambient | 0.3 |
| Color      Y (12.7 mm cell) R           N | 13 1.0 0.3 | 9.9 0.9 0 | 8.6 0.6 0.2 |

It can be seen that conventional decolorization does not improve the degree of decolorization despite two successive treatments (Comparisons 3 and 4). In Examples 3 to 7, the starting material used is an oil which had undergone two successive conventional decolorizations and is decolorized to a considerable extent by a single passage.

Examples 8–11

These Examples relates to the decolorization of *Hevea brasiliensis* oil which has the following fatty acid composition:

| Fatty acids | % |
|---|---|
| C16:0 | 8.8 |
| C18:0 | 8.7 |
| C18:1 | 24.9 |
| C18:2 | 38.6 |
| C18:3α | 16.7 |
| Others | 2.3 |

The working conditions and results obtained are set out in Tables 3 and 4 below.

TABLE 3

| Example | Comparison 5 | Comparison 6 | 8 | 9 |
|---|---|---|---|---|
| Sample (g) | After | 150 | 150 | 150 |
| n-Hexane (ml) | 1 | 450 | 450 | 450 |
| Adsorbent (type) | conventional decolorization | a | a + b | a + b + c |
| Proportions (%) of the components of the adsorbent | | 100 | a:80 b:20 | a:50 b:20 c:30 |
| Quantity (g) of adsorbent | | 75 | 75 | 75 |
| Type of column | | Glass | Glass | Glass |
| Diameter (mm) | | 27 | 27 | 27 |
| Height (cm) | | 25 | 25 | 25 |
| Pressure (bar) | | Ambient | 0.2 | 0.2 |
| POV (meqO₂/kg) | 0.66 | 1.05 | 0.64 | 0.96 |
| Color       Y (25.4 mm cell) R | 68 13.3 | 24.5 3.9 | 2.2 0.6 | 2.2 0.5 |

TABLE 4

| Example | Comparison 7 | Comparison 8 | 10 | 11 |
|---|---|---|---|---|
| Sample (g) | 100 | 100 | 100 | 100 |
| n-Hexane (ml) | 900 | 900 | 900 | 900 |
| Adsorbent (type) | b | f | a + b + c | d + b + f |
| Proportions (%) of the components of the adsorbent | 100 | 100 | a:50 b:20 c:30 | d:33.3 b:33.3 f:33.3 |
| Quantity (g) | 50 | 50 | 50 | 50 |
| Type of column | Glass | Glass | Glass | Glass |
| Diameter (mm) | 50 | 50 | 50 | 50 |
| Height (cm) | 10 | 10 | 10 | 10 |
| Pressure (bar) | 0.2 | Ambient | Ambient | Ambient |
| Color       Y (25.4 mm cell) R | 6.1 1.5 | 3.1 0.9 | 2.4 0.7 | 0.5 0 |

It can be seen that the decolorization process according to the invention using a mixture of adsorbents gives distinctly better results (Examples 8 and 9 in conjunction with Comparison 6; Example 10 in conjunction with Comparison 7; Example 11 in conjunction with comparisons 7 and 8) than those obtained where only one of the adsorbents is used under the same working conditions. In addition, the mixtures of adsorbents provide for intensive decolorization which cannot be achieved by conventional decolorization (Comparison 5).

Examples 12–15

The parameters of the process and the results relating to the decolorization of kiwi seed oil are set out in Table 5 below.

The oil used has the following fatty acid composition:

| Fatty acids | % |
|---|---|
| C16:0 | 4.9 |
| C18:0 | 2.6 |
| C18:1 | 11.2 |
| C18:2 | 14.9 |
| C18:3α | 63.8 |
| Others | 2.6 |

TABLE 5

| Example | Comparison 9 | 12 | 13 | 14 | 15 |
|---|---|---|---|---|---|
| Sample (g) | After | 200 | 200 | 200 | 15000 |
| n-Hexane (ml) | 1 | 1800 | 1800 | 1800 | 135000 |
| Adsorbent b (%) | conventional decolorization | 50 | 25 | 60 | 55 |
| f (%) | | 50 | 75 | 40 | 45 |
| Quantity (g) of adsorbent | | 50 | 50 | 50 | 5000 |
| Type of column | | Glass | Glass | Glass | Glass |
| Diameter (mm) | | 50 | 50 | 50 | 225 |

TABLE 5-continued

| Example | Comparison 9 | 12 | 13 | 14 | 15 |
|---|---|---|---|---|---|
| Height (cm) | | 10 | 10 | 10 | 80 |
| Pressure (bar) | | Ambient | Ambient | Ambient | Ambient |
| Color Y | 68 | 9.6 | 11.2 | 7.3 | 5.4 |
| (133.35 mm  R | 8.1 | 1.2 | 1.3 | 1.0 | 0.8 |
| cell)  N | 1.7 | 0.2 | 0.6 | 0.2 | 0.2 |

It can be seen that the adsorbent mixture of montmorillonite and active carbon achieves substantial decolorization of a strongly colored kiwi seed oil which cannot be achieved to the same extent by the conventional method (Comparison 9).

Examples 16–19

Bilberry oil (16), elder oil (17), calendula oil (18) and fish oil (19) are decolorized under the conditions and with the results set out in Table 6 below.

These oils have the following fatty acid compositions:

| Fatty acids | % | | | |
|---|---|---|---|---|
| | 16 | 17 | 18 | 19 |
| C16:0 | 4.1 | 7.4 | 3.2 | 17.6 |
| C16:1 | — | — | — | 4.7 |
| C18:0 | 1.1 | 2 | 2.1 | 4.5 |
| C18:1 | 23.2 | 14 | 4.9 | 21.8 |
| C18:2 | 35.9 | 41 | 31.3 | 1.4 |
| C18:3α | 34.3 | 30.1 | 0.6 | 0.4 |
| C18:3Δ8, 10, 12 | — | — | 48 | — |
| C20:1 | — | — | — | 2.5 |
| C20:5 | — | — | — | 6.2 |
| C22:6 | — | — | — | 23.9 |
| Others | 1.3 | 5.5 | 9.9 | 17 |

TABLE 6

| Example | 16 | 17 | 18 | 19 |
|---|---|---|---|---|
| Sample 100 | 650 | 650 | 1000 | 100 |
| n-Hexane (ml) | 2600 | 2600 | 3000 | 400 |
| Adsorbent (type) | a + b + g | a + b + c | a + b + c | a + b + g |
| Proportions (%) of the components of the adsorbent | a:70 b:20 g:10 | a:60 b:20 c:20 | a:60 b:20 c:20 | a:60 b:20 g:20 |
| Quantity (g) of adsorbent | 330 | 330 | 660 | 50 |
| Type of column | Glass | Glass | Glass | Glass |
| Diameter (mm) | 27 | 35 | 50 | 27 |
| Height (cm) | 25 | 55 | 100 | 25 |
| Pressure (bar) | 0.2 | 0.8 | 1.5 | 0.2 |
| Color Y (25.4 mm cell) | 0.3 | 0.5 | 12.5 | 0.8 |
| R | 0.1 | 0.05 | 0.6 | 0.1 |
| Comparison 10, Color after 1 conventional decolorization (25.4 mm cell) Y | 31 | 7 | >40 | 24 |
| R | 5.3 | 1 | 6.8 | 2.4 |

It can be seen that the process according to the invention using a mixture of adsorbents produces a distinct improvement in decolorization by comparison with conventional decolorization.

Example 20

The parameters of the process and the results of the decolorization of butane-2,3-diol diester prepared in accordance with Example 1 of European patent application Publication No. 0 465 698 are set out in Table 7 below:

TABLE 7

| Example | Comparison 11 | 20 |
|---|---|---|
| Sample (kg) | 1 | 21 |
| n-Hexane (l) | conventional decolorization | 84 |
| Adsorbent (type) | | f + b |
| Proportions (%) of the components of the adsorbent | | f:55 b:45 |
| Quantity (kg) of adsorbent | | 8.4 |
| Type of column | | Glass |
| Diameter (mm) | | 225 |
| Height (cm) | | 80 |
| Throughput (l/h) | | 23 |
| Color | | |
| (25.4 mm cell)  Y | 23.3 | — |
| R | 4.9 | — |
| B | 0.5 | — |
| (133.4 mm cell)  Y | 37.8 | 0.8 |
| R | 52.8 | 0.1 |
| B | 32 | 0 |

It can be seen that the process according to the invention achieves substantially complete decolorization. By contrast, the same result is not achieved by conventional decolorization.

Examples 21–22

The nomenclature used in these Examples is that of the "Cosmetic, Toiletry and Fragrance Association, Inc. Washington D.C." (CFTA) in its French translation. 21. To produce a cosmetic cream in the form of an oil-in-water emulsion, the components of the lipidic phases A and B are separately mixed and heated to 70° C., after which phase B is incorporated in phase A. The aqueous phase C is prepared by mixing these components and heating to 70° C. The lipidic phases A and B are added to the aqueous phase C at 70° C. while stirring at average speed. The mixture of the two phases is homogenized, stirred at approximately 100 r.p.m. and then left to cool to 35°–40° C.

The additives are incorporated at that temperature, after which the mixture is left to cool to ambient temperature with slow stirring, the stirrer being switched off when the product is semifluid (at approx. 25° C.).

The cream has the following composition:

| | % |
|---|---|
| Phase A (lididic) | 12.1 |
| PEG-10 isocetyl ether monostearate | 4.5 |
| Steareth-21 | 1.5 |
| Glycerol stearate | 2.6 |
| Cetoaryl alcohol | 1.5 |
| Isodecyl laurate | 2 |
| Phase B (lipidic) | 6.3 |
| Decolored cumin oil of Example 1 | 6 |
| Carbomer 934 (crosslinked acrylic acid polymer) | 0.3 |
| Phase C (aqueous) | 79.8 |
| Water | 74.7 |
| Glycerol | 5 |

-continued

|  | % |
|---|---|
| Ethylenediamine tetraacetate (EDTA) | 0.1 |
| Additives | 1.8 |
| Phenoxyparabene | 0.6 |
| Silmethicone | 0.1 |
| Trimethamine (30% aqueous solution) | 0.8 |
| Perfume | 0.3 |
|  | 100 |

22. Decolored *Lesquerella* oil is used as a substitute for castor oil in an anhydrous lipstick.

The product is obtained in the same way as in Example 21, but without homogenization, by hot mixing (approx. 70° C.) and gradual cooling with slow stirring.

It has the following composition:

|  | % |
|---|---|
| *Lesquerella* oil decoloured in accordance with Example 7 | 27.45 |
| Castor oil | 30.5 |
| Beeswax | 10.5 |
| Candelilla wax | 7.5 |
| Ozocerite | 5.5 |
| Isopropyl lanolate | 5 |
| Colourants | 13.55 |

Example 23

A milk product for infants to be reconstituted by addition of water is prepared in powder form by mixing the aqueous and lipidic phases, concentration by evaporation and spray drying in a tower under controlled conditions.

The composition of the dry matter is as follows:

| Ingredients | % |
|---|---|
| Mixture of fats containing lecithin | 26 |
| Fish oil decoloured in accordance with Example 19 | 0.6 |
| Lactose and maltodextrin | 60 |
| Lactic proteins | 11 |
| Mineral salts | 1.6 |
| Vitamins and oligoelements | 0.8 |
|  | 100 |

We claim:

1. A process for decoloring fatty acid esters comprising passing a solution of a fatty acid ester dissolved in an apolar solvent through a column containing a mixture of particulate montmorillonite having a particle size of from 5$\mu$ to 60$\mu$ and a particulate material selected from the group consisting of silica gel and active carbon, obtaining the solution passed through the mixture and then, eliminating the solvent from the ester.

2. A process for decoloring fatty acid esters comprising passing a solution of a fatty acid ester dissolved in an apolar solvent through a column containing a mixture of particulate montmorillonite having a particle size of from 60$\mu$ to 250$\mu$ and a particulate material selected from the group consisting of silica gel and active carbon, obtaining the solution passed through the mixture and then, eliminating the solvent from the ester.

3. A process for decoloring fatty acid esters comprising passing a solution of a fatty acid ester dissolved in an apolar solvent through a column containing a mixture of particulate montmorillonite, wherein 40% to 60% by weight of the montmorillonite has a particle size of from 5$\mu$ to 60$\mu$ and from 60% to 40% by weight of the montmorillonite has a particle size of from above 60$\mu$ to 250$\mu$, and a particulate material selected from the group consisting of silica gel and active carbon, obtaining the solution passed through the mixture and then, eliminating the solvent from the ester.

4. A process according to claim 1, 2 or 3 wherein the mixture contains active carbon having a particle size of from 100$\mu$ to 500$\mu$.

5. A process according to claim 1 wherein the mixture contains, by weight, from 10% to 60% montmorillonite and up to 80% silica gel.

6. A process according to claim 5 wherein the mixture contains, by weight, approximately 50% montmorillonite and approximately 50% silica gel.

7. A process according to claim 5 or 6 wherein 40% to 60% by weight of the montmorillonite has a particle size of from 5$\mu$ to 60$\mu$ and from 60% to 40% by weight of the montmorillonite has a particle size of from above 60$\mu$ to 250$\mu$.

8. A process according to claim 5 wherein the mixture further contains active carbon in an amount of from 30% to 60% by weight.

9. A process according to claim 1 wherein the mixture contains, by weight, from 20% to 70% montmorillonite and from 30% to 80% active carbon.

10. A process according to claim 1 wherein the mixture further contains a diatomaceous earth.

11. A process according to claim 10 wherein the diatomaceous earth is selected from the group consisting of diatomite and perlite.

12. A process according to claim 10 wherein the mixture contains the diatomaceous earth in an amount of up to 30% by weight.

13. A process according to claim 1 wherein the solvent is a food-acceptable aliphatic hydrocarbon and the ester and solvent are in a ratio by weight of ester to solvent of from 1:2 to 1:16.

14. A process according to claim 1 wherein the ester is passed through the adsorbent in a ratio by weight of ester to adsorbent of from 0.5:1 to 5:1.

15. A process according to claim 1 further comprising, prior to eliminating the solvent from the ester, rinsing the mixture with an apolar solvent, obtaining a rinse from the mixture, combining the rinse with the solution obtained from the mixture.

16. A process according to claim 1 wherein the solvent is eliminated by evaporation in vacuo.

17. A process according to claim 1 wherein the ester is selected from the group consisting of animal oils and vegetable oils.

18. A process according to claim 1 wherein the ester is fish oil.

19. A process according to claim 1 wherein the ester is an oil selected from the group of consisting of cumin, calendula, bilberry, elder, coffee, kiwi and *Hevea brasiliensis* oils.

20. A process according to claim 1 wherein the ester is an oil obtained from envelopes of yeast.

21. A process according to claim 1 wherein the ester is *Lesquerella* oil.

22. A process according to claim 1 wherein the ester is a butanediol diester.

23. A process according to claim 1 wherein the ester is butane-2,3-diol diester.

* * * * *